United States Patent [19]

Berry, Jr. et al.

[11] Patent Number: 5,178,463
[45] Date of Patent: Jan. 12, 1993

[54] METHOD OF AND APPARATUS FOR MEASURING COOLANT QUENCHING RATES

[75] Inventors: James S. Berry, Jr., Savannah, Tenn.; Dennis G. Brooks, Florence; Thomas J. Johnston, Rogersville, both of Ala.

[73] Assignee: Reynolds Metals Company, Richmond, Va.

[21] Appl. No.: 807,029

[22] Filed: Dec. 12, 1991

[51] Int. Cl.$^5$ .......................................... G01N 25/00
[52] U.S. Cl. ..................................... 374/43; 364/557; 374/55
[58] Field of Search ................ 374/43, 54, 55, 29; 364/557

[56] References Cited

U.S. PATENT DOCUMENTS

| | | | |
|---|---|---|---|
| 2,587,622 | 3/1952 | Jaffe | 374/43 |
| 2,717,515 | 9/1955 | Pesante | 374/43 |
| 3,620,068 | 11/1971 | Cary et al. | 374/43 |
| 4,024,751 | 5/1977 | Potrzebowski | 374/43 |
| 4,036,051 | 7/1977 | Fell et al. | |
| 4,093,020 | 6/1978 | Schieber | 374/43 X |
| 4,106,331 | 8/1978 | Bunton et al. | |
| 4,395,380 | 7/1983 | Rosh | 374/54 X |
| 4,412,752 | 11/1983 | Cellitti et al. | |
| 4,420,965 | 12/1983 | Farkas et al. | 374/43 |
| 4,563,097 | 1/1986 | Katafuchi | |
| 4,636,089 | 1/1987 | Schumann | |
| 4,840,495 | 6/1989 | Bonnefoy | |

FOREIGN PATENT DOCUMENTS

| | | | |
|---|---|---|---|
| 1076775 | 2/1984 | U.S.S.R. | 374/43 |
| 1278696 | 12/1986 | U.S.S.R. | 374/43 |

Primary Examiner—Daniel M. Yasich
Attorney, Agent, or Firm—Alan M. Biddison

[57] ABSTRACT

An apparatus and method for measuring coolant quenching rates includes a metallic disk supported on a ceramic tube, the metallic disk including a plurality of thermocouples therein. The metallic disk is heated from above by a torch and coolant is sprayed on the underside of the disk. Changes in temperature throughout the metallic disk are detected by the thermocouples to measure various quenching parameters. The metallic disk may be surrounded by insulating material to maintain heat flow through the disk in a predetermined manner. By heating, insulating and cooling the metallic disk, temperature measurements can be quantified into heat transfer rates to investigate various heat transfer mechanisms and different types of coolants.

22 Claims, 7 Drawing Sheets

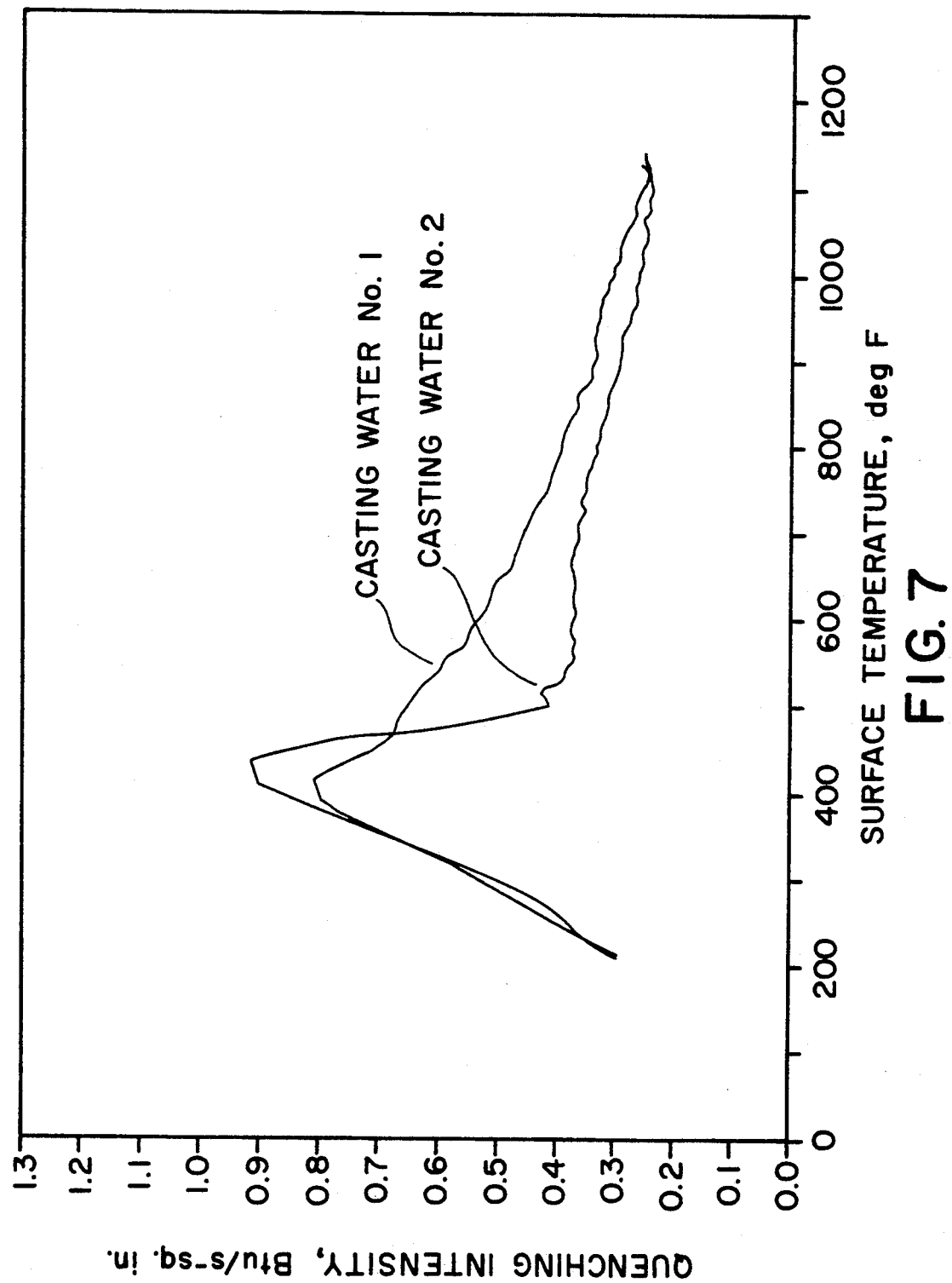

METHOD OF AND APPARATUS FOR MEASURING COOLANT QUENCHING RATES

FIELD OF THE INVENTION

The present invention is directed to a method of and apparatus for measuring coolant quenching rates. The method includes monitoring the temperature profile of a thickness of a given material when subject to quenching by a particular quenching media. The measuring apparatus permits development of quenching curves which quantify average heat transfer rates and changes between different types of heat transfer mechanisms.

BACKGROUND OF THE INVENTION

In various metallurgical processes such as casting, rolling, forming, etc., the time/temperature profile of the working piece must be precisely controlled. Quenching or cooling media are often used to control temperature, and, accordingly, the cooling power or quenching intensity of these media need to be precisely monitored and controlled.

Furthermore, the heat transfer mechanisms of quenching can change depending on the temperature of the piece being worked. When the surface temperature is much higher than the boiling temperature of the liquid, heat transfer is via "film boiling" in that a continuous film of vapor is maintained between the metal surface and the coolant. In this heat transfer phenomena, the heat transfer rates are relatively low and stable. As the metal surface cools, it will eventually reach a temperature at which the coolant will contact the surface and heat transfer rates will increase rapidly. The heat transfer rates peak during the "nucleate boiling" regime where a large number of steam bubbles are created and easily escape allowing more liquid coolant to come into contact with the surface. As the surface temperature continues to decrease, it eventually cools below the boiling temperature of the coolant and nucleate boiling ceases, heat transfer then is predominantly by convection, and heat transfer rates rapidly decrease.

Quenching media can include water, aqueous solutions of salts or glycols, water/oil emulsions, molten salts, etc. Given the wide range of quenching media available for heat treating processes, a need has developed to measure the quenching intensity of the quenching media throughout the temperature range of a workpiece and initiation of nucleate boiling.

The prior art has provided different systems and devices for evaluating or testing different types of quenching parameters. U.S. Pat. No. 4,636,089 to Schumann discloses a system where a test body is inserted into a bath. The heat energy required to maintain the temperature of the test body constant is used as a measure of the quenching intensity of the bath.

U.S. Pat. No. 4,563,097 to Katafuchi discloses another method for evaluating the cooling performance of a heat treatment agent. In this method, a sensor is placed into a heat treatment agent which is heated to a predetermined temperature. The voltage and current applied to the sensor during the heating step is monitored. A comparison of the acquired data to predetermined data permits an evaluation of the performance of a heat treating agent.

U.S. Pat. No. 4,412,752 to Cellitti et al. discloses a system including a probe and sensor that are heated to a predetermined temperature and then immersed in a quenching medium. Cooling data obtained from the probe and sensor are applied to a computer for comparison with predetermined values.

U.S. Pat. No. 3,620,068 to Cary et al. discloses a testing apparatus for measuring and recording changes in quenching media temperature. The testing apparatus includes thermocouples for sensing temperature of inflowing and outflowing quenching fluid during quenching of a specimen.

It is the purpose of the present invention to provide a method and apparatus for measuring the quenching intensity or cooling power of various liquid media, particularly with regards to water, aqueous solutions and water/oil emulsions during the casting and hot rolling of metals such as aluminum and aluminum alloys. The information obtained from the present invention can be used for quality control, for evaluating different quenching media, and to correlate the effects of changes in operations and quenching media compositions with quenching power for purposes of process improvement and the development of improved quenching media.

The prior art discussed above does not teach or fairly suggest the inventive method and apparatus for measuring the quenching intensity or cooling power of various liquid media which monitors the temperature profile of a heated sample during cooling.

SUMMARY OF THE INVENTION

It is accordingly a first object of the present invention to provide a method of and apparatus for measuring coolant quenching rates.

It is a further object of the present invention to provide a method of and an apparatus for measuring coolant quenching rates that permits measurement of quenching intensity of various coolants and temperature ranges over which different heat transfer mechanisms occur, such as nucleate and film boiling.

It is a still further object of the present invention to provide a method of and apparatus for measuring coolant quenching rates which permits evaluating different quenching media for purposes of quality control and correlating changes in operating parameters and quenching media compositions with quenching power for improvements in product quenching and quality.

Other objects and advantages of the present invention will become apparent from the following description.

In satisfaction of the foregoing objects and advantages, there is provided an apparatus for measuring coolant quenching rates, the apparatus including a heating means for raising the temperature of a metallic disk to a predetermined temperature, means for insulating the metallic disk such that only one surface is exposed and cooling means for applying a coolant to the exposed surface. Also included are means to detect temperature along a given dimension of the metallic disk to facilitate measuring coolant quenching intensity and support and barrier means for supporting the disk and confining the coolant to the exposed surface.

Also provided by the present invention is a method for measuring coolant quenching rates which comprises measuring the temperature of the metallic disk throughout the quenching cycle and calculating the heat flux through the disk using a heat transfer model. The heat flux or quenching intensity may be plotted as a function of the surface temperature of the metallic disk to generate a quenching curve. The quenching curve permits analysis of coolant quenching parameters such as quenching intensity of various coolants or a break through temperature at which nucleate boiling initiates.

In particular, the apparatus comprises a metallic disk approximately 1" thick by 3" in diameter. Small holes are drilled into the disk from the edge for insertion of thermocouples. The thermocouple junctions are located at three depth positions along the centerline axis of the disk. The temperature profile being measured by these probes is used in the heat transfer analysis.

Coolant or quenching media is sprayed from below the disk by a nozzle such that the spray pattern covers the lower surface of the disk. The disk is then heated by means of a torch. An intense flame is required to heat the disk through the nucleate boiling range.

The disk is heated to approximately 100° F. above the highest temperature of interest. At this point, the flame is removed and the top and side surfaces are insulated. The disk begins to cool slowly because of low heat transfer rates during film boiling. Finally, when the surface of the disk becomes cool enough, the vapor barrier breaks down and the coolant makes contact with the surface. Nucleate boiling begins and heat transfer rates are high. Once the temperature of the surface decreases below the saturation temperature of the coolant, boiling ceases and heat transfer rates decrease sharply. The entire measurement takes less than 5 minutes to complete. Typically, 3 to 5 runs are conducted per test.

Control means are provided to control flow of quenching media and heating of the metallic disk by analyzing electrical signals from temperature, pressure and flow sensors.

A plot is generated of the heat transfer rate (quenching intensity) versus surface temperature. From the data analysis, two important qualities of the coolant may be investigated: (1) The cooling power or quenching intensity of the coolant, i.e., at what rate can it extract heat from a metallic surface at various temperatures, and (2) The "breakthrough" temperature, i.e., at what temperature does the vapor film break down and nucleate boiling begin.

BRIEF DESCRIPTION OF DRAWINGS

Reference is now made to the Drawings accompanying the application wherein:

FIG. 7 shows another quenching curve used to monitor different water qualities during metallurgical processing.

DESCRIPTION OF THE PREFERRED EMBODIMENTS

The present invention is concerned with a method of and apparatus for measuring coolant quenching rates. The inventive apparatus and method facilitate measuring heat transfer parameters, especially at elevated temperatures, such as those encountered under actual rolling and casting conditions in metallurgical processes. Temperatures of interest with aluminum, broadly speaking, can range from about 200° F. to about 1200° F. Temperatures of special interest are around 900° F. to about 1200° F. which are within the normal quenchant's film boiling zone. For instance, temperatures encountered during hot rolling of aluminum can range between about 900° F. and about 1050° F.

The inventive method and apparatus provide improvements over prior art systems by providing quantification of heat flux as a result of spray quenching using different types of coolants and/or lubricants. Using the inventive apparatus and method, breakthrough temperatures such as the temperature at which nucleate boiling begins or ends can be determined for various quenching intensities and types of coolants.

Figure 1:
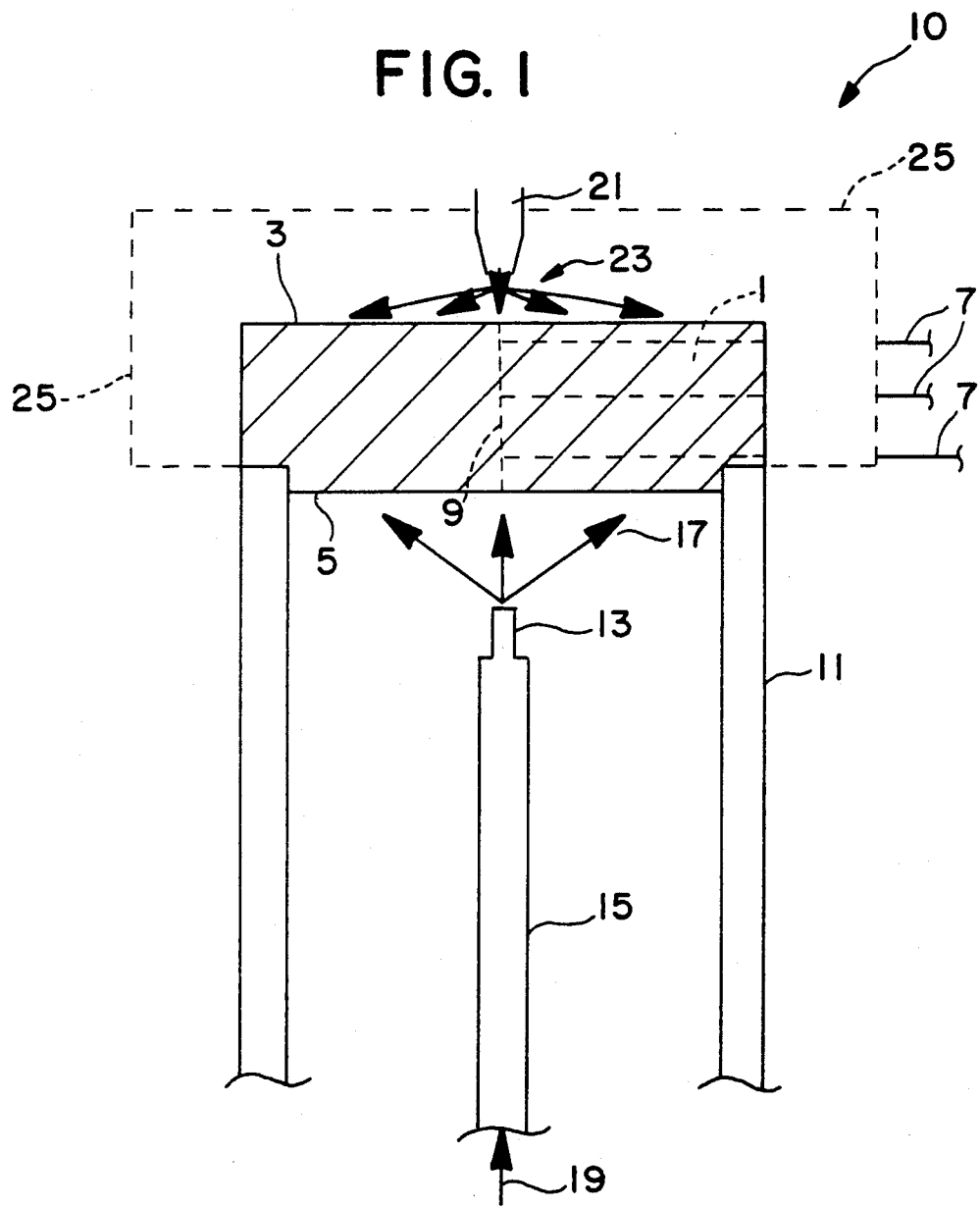
FIG. 1 shows a schematic diagram partly in cross-section showing apparatus components of the present invention.

Referring to FIG. 1, an apparatus for measuring coolant quenching rates is generally designated as reference numeral 10 and includes a metallic disk 1 of approximately 1" thickness by 3" diameter having a top surface 3 and a bottom surface 5. The disk 1 should be constructed of a metal with a relatively high melting point and high thermal conductivity such as copper. The circular shape of the disk sample 1 and high conductivity facilitate obtaining an essentially one-dimensional temperature gradient across the thickness of the disk sample. The disk sample 1 is shown being fitted with three thermocouples 7. Three thermocouples 7 should be of small diameter, 1/16" or less, and inserted into the disk 1 via machined holes in the side surface of the disk (not shown), and should be precisely aligned along the center axis line 9 of the disk. Although three thermocouples are shown at a given configuration, more or less thermocouples may be used at various spacings along the axis 9 of the disk 1 at precisely known distances from the bottom surface of the disk. One advantage of placing the thermocouples inside the disk is that they are protected from the intense heat of the torch used in a preferred embodiment to heat the disk. Also, means other than thermocouples can be used to measure the changes of temperature with time.

The metallic disk 1 is aligned and supported by placement upon a tube 11 of low thermal conductivity material, such as quartz or ceramic. A spray nozzle 13 aligned axially with the tube 11 is connected via tubing 15 to a reservoir of cooling or quenching media (not shown) and provides a spray 17 of coolant 19 supplied through tubing 15 to the bottom surface 5 of the metallic disk 1. The flow rate of coolant and the spacing between the nozzle 13 and disk 1 are adjustable so that the spray pattern covers the entire bottom surface 5 of the disk 1. The coolant, after having contacted the metallic surface is contained within the tube 11 and drains to a spent coolant reservoir (not shown) and discarded.

Preferably, the flow of coolant is started prior to heating of the disk 1. If the lower surface is not cooled prior to heating of the disk, there is an increased possibility of the bottom surface of the disk getting too hot so that particles in the coolant will fuse to the surface thereby altering the heat transfer characteristics of the disk.

The metallic disk 1 is rapidly heated to the desired temperature by use of a gas torch 21, such as an oxyacetylene or propane torch, the arrows 23 representing heating by the torch flame. Flame impingement is preferred over resistance or other electrical heating to rapidly achieve the high temperatures used in the process. The disk should be heated to a temperature above the upper temperature of interest by approximately 100° F. The torch is then removed and the sides and top of the disk are insulated by placement of insulating material 25 immediately after the torch 21 has been raised. The insulating material may be rigid or flexible and may comprise a type such as Kaowool. The insulated side and top surfaces, the cooling of the bottom surface and the high thermal conductivity of the metallic disk result in the heat flow through the disk to be essentially one dimensional from the top of the disk to the bottom. The one dimensional flow of heat greatly facilitates and simplifies the calculation of quenching rates.

It should be noted that the insulation material 25, in addition to covering the disk 1, can cover upper portions of the side wall of the tube 11. Slits may be provided in the insulation for the leads connected to the thermocouples 7. The objective is reduce the amount of heat lost through the top and sides of the disk 1. Preferably, the disk 1 is provided with an annular seat, as illustrated in FIG. 1, that allows the disk to sit in the top of tube 11. The surface of the seat, in one embodiment, is roughened to reduce heat flow between the disk 1 and the tube 11.

It is desireable to have the disk 1 removable from the tube 11 to facilitate cleaning of the disk's lower surface. Any contaminant or oxide build up on this surface has a tendency to reduce measurement accuracy.

From the temperature profile through the thickness of the disk 1 as measured by the thermocouples 7, the temperature of the bottom surface of the disk and the heat flux through the disk can be calculated throughout the quenching cycles by the use of suitable heat transfer models, which are known in the art. The temperature data should be sampled at a rate of 5 hertz or greater but other intervals may also be used. The heat flux through the disk is approximately equal to the rate of heat removal by the coolant, i.e., the quenching intensity.

Under steady-state conditions, heat flow is calculated using the following equation:

$$Q = \frac{-kA(\Delta t)}{x}$$

Where "k" is the thermal conductivity of the disk, "A" is the surface area of the disk, "$\Delta t$" is the temperature gradient across the disk, and "x" is the disk thickness. The quenching curve is presented as a plot of heat flux or quenching intensity as a function of the bottom surface temperature of the metallic disk.

Figure 2:
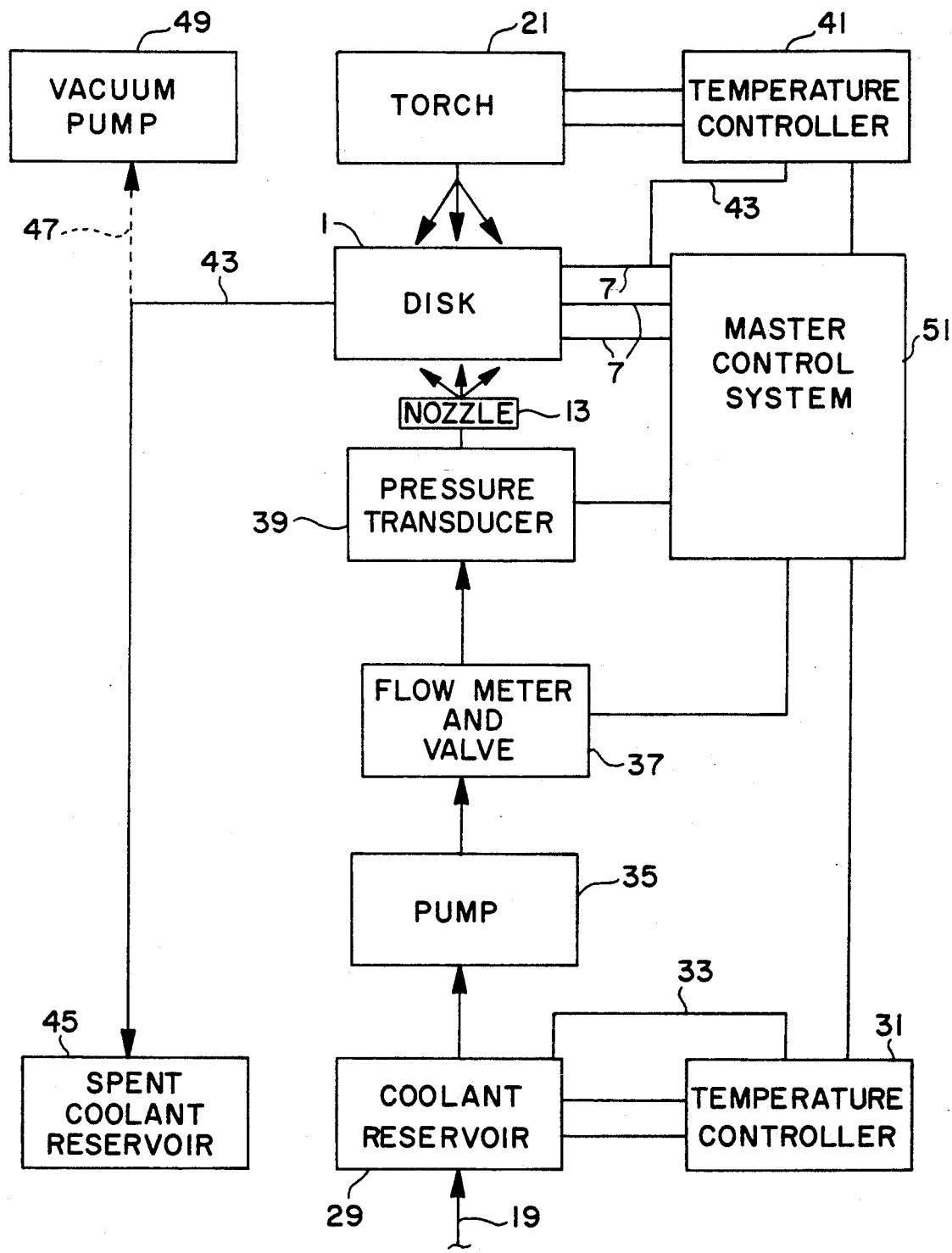
FIG. 2 shows a schematic flow diagram illustrating an exemplary method using apparatus components of the present invention.

An exemplary method and additional measuring apparatus components are shown by the block diagram of FIG. 2. The coolant or quenching media 19 is charged to a fresh coolant reservoir 29 where the temperature is controlled using a temperature controller 31 and control thermocouple 33. The coolant is pumped using a pump 35 such as a constant volume pump through a flow meter and valve 37. The control valve 37 is used to control the flow rate of the coolant. The pressure in the spray nozzle is monitored using a pressure transducer 39. The spray nozzle 13 and metallic sample disk 1 are shown in greater detail in FIG. 1. The gas torch 21 is automatically controlled by means of a temperature controller 41 and control thermocouple 43. The spent coolant is routed to the spent coolant reservoir 45. Vapors 47 from the boiling coolant are collected and removed using a vacuum pump 49. Electrical signals from the temperature, pressure and flow sensors are sampled and analyzed by an automatic data acquisition and master control system 51 at a frequency of approximately 5 hertz. The master control system 51 may be a computing or microprocessing means capable of controlling temperature controllers 31 and 41, and flow meter valve 37 to provide a single control system during testing. The entire testing period may be about 5 minutes but can vary depending on the type of quenching test performed. Multiple tests are conducted for each coolant to determine variability and statistical confidence intervals.

Figure 3:
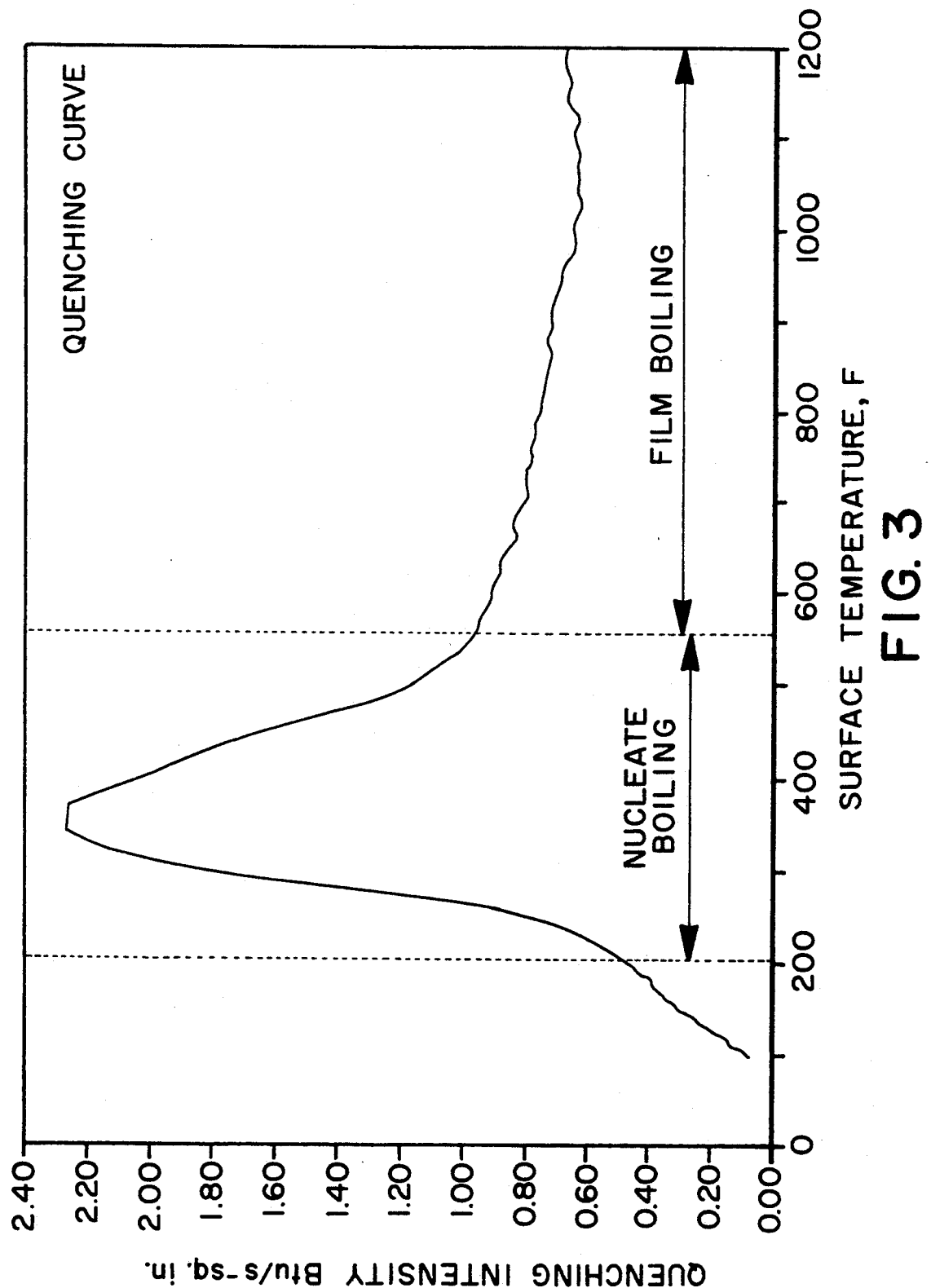
FIG. 3 shows a typical quenching curve obtained according to the present invention.

The quenching curve typically takes the form shown in FIG. 3. By plotting quenching intensity versus surface temperature, the temperature ranges of film boiling, i.e., low and stable heat transfer rates, and nucleate boiling, i.e., contact of the coolant with the surface resulting in high boiling rates and high heat transfer rates, can be observed. Important attributes of the quenching curve can be quantified such as average heat transfer rates over the temperature range of interest and the temperature range over which the heat transfer mechanism changes from nucleate boiling to film boiling.

The following examples illustrate monitoring different types of quenching parameters when using the apparatus for and method of measuring coolant quenching rates. However, the invention is not considered to be limited thereto as obvious variations thereon will be apparent to those skilled in the art.

EXAMPLE 1

Figure 4:
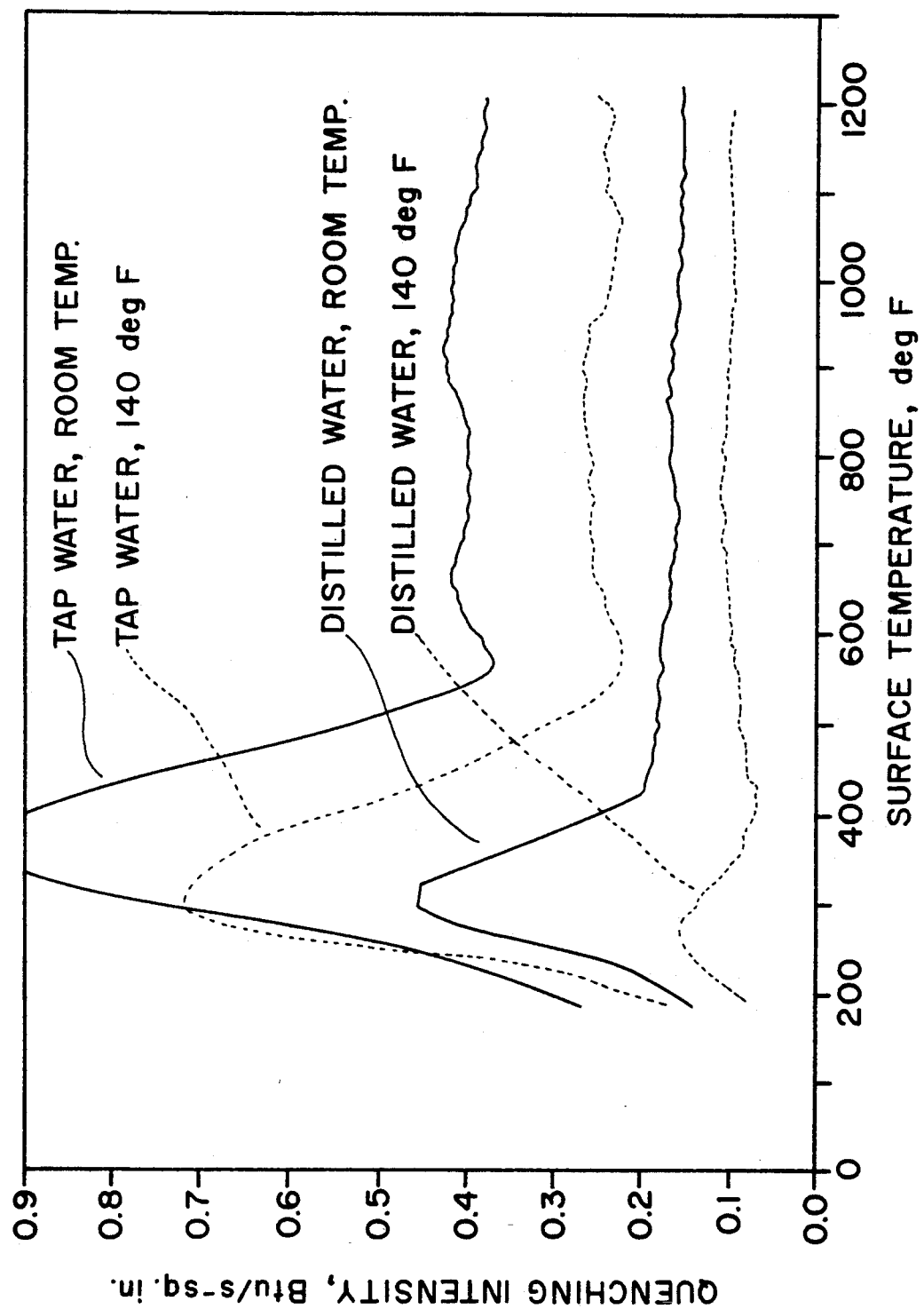
FIG. 4 shows a quenching curve utilizing different quenching media.

The apparatus described above was used to measure the quenching curves of water as a function of water temperature and water quality. The results are shown in FIG. 4 which show that quenching intensity decreases with increasing purity and increasing temperature. Such information contributes in developing, monitoring and controlling aqueous quenching media as applied to metallurgical processes.

EXAMPLE 2

Figure 5:
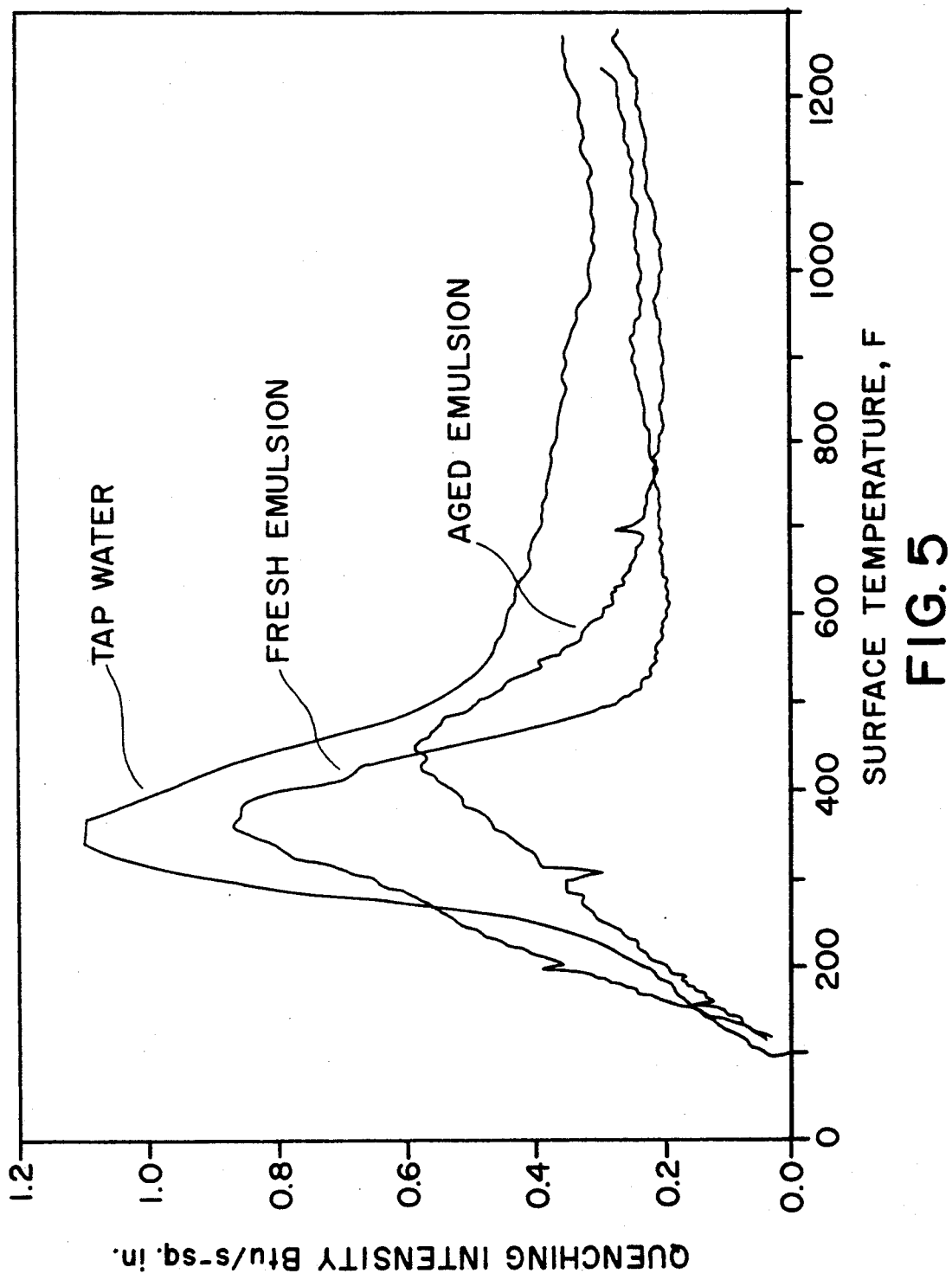
FIG. 5 shows another quenching curve comparing different quenching media.

The apparatus described was used to measure the quenching curves of various quenching media. The quenching curves of water, an aged hot rolling emulsion and a freshly-prepared hot rolling emulsion are compared in FIG. 5. This demonstrates that the apparatus can be used to differentiate between different quenching media and monitor the changes in quenching intensity over time. As the emulsion aged during the hot rolling process, peak quenching rates decreased. This information can be used to monitor effectiveness of quenching media which is repeatedly used.

EXAMPLE 3

Figure 6:
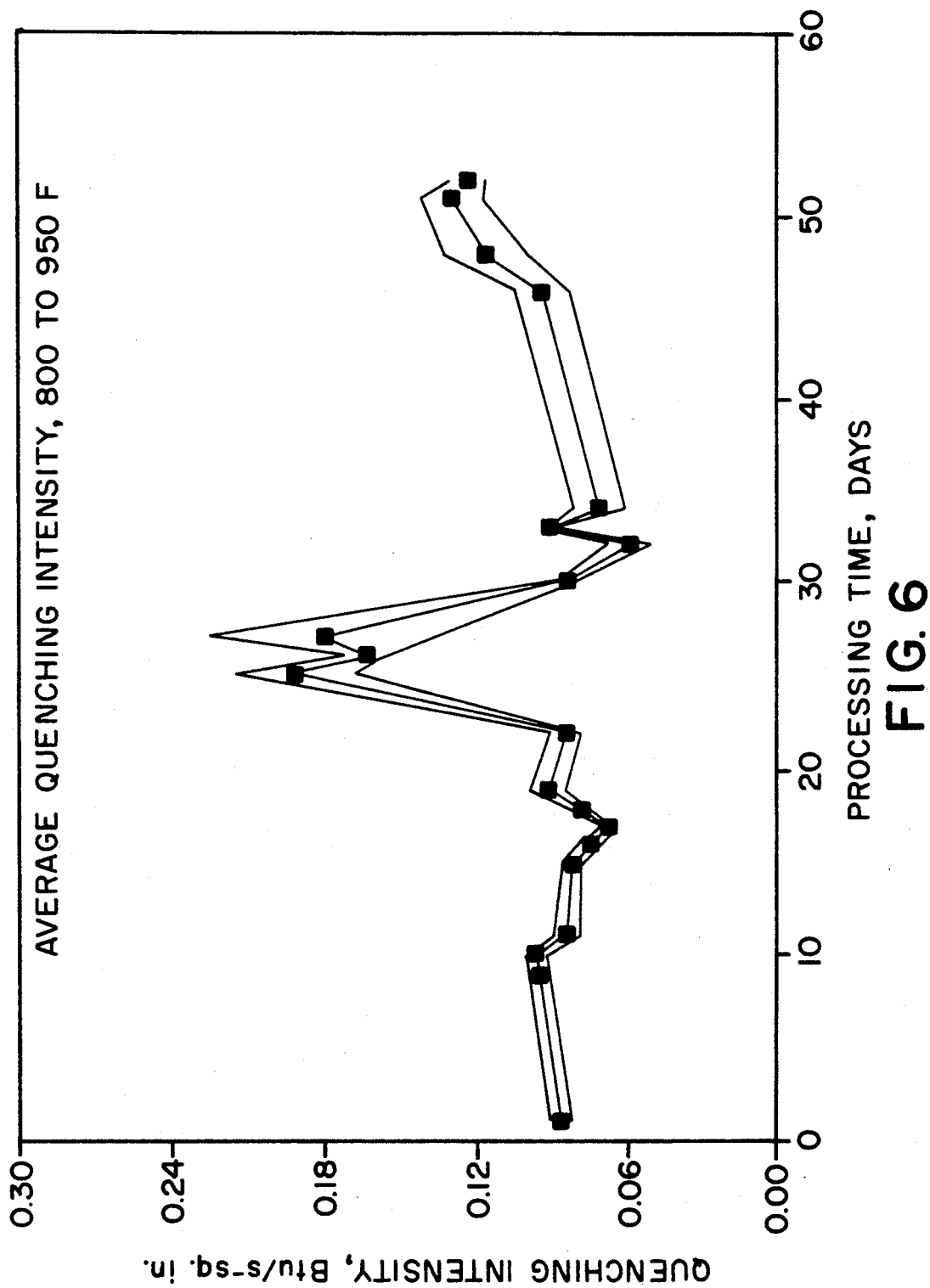
FIG. 6 shows a curve monitoring quenching intensity over a given period of time.

The apparatus described above was used to monitor the average quenching intensity of an oil/water emulsion used in the hot rolling of aluminum alloy. The average quenching intensity was determined from an integration of the quenching curve over the temperature range typically encountered by an ingot during the rolling process. Twenty-one samples of rolling emulsions were tested over a period of 52 days. The average quenching intensity as a function of days of operation is plotted in FIG. 6. The precision of the measurements is also plotted (±1 standard deviation). This demonstrates that the apparatus can be used to measure the process variability of quenching intensity which would have application in quality assurance and quality control.

EXAMPLE 4

The apparatus described above was used to measure the quenching intensity of contact water from two separate facilities used to cast aluminum ingot. Results are given in FIG. 7. Significant differences were measured in the quenching curves that would affect the rate at which the ingot is cooled during casting which, in turn, could affect overall ingot quality. Chemical analysis revealed that the contact water from the two facilities differed regarding hardness and oil content as follows:

|  | Hardness (as ppm CaCO$_3$) | Oil & Grease ppm |
| --- | --- | --- |
| Casting Water No. 1 | 175.7 | 4.3 |
| Casting Water No. 2 | 99.4 | <1.0 |

As can be seen from FIG. 7, the casting water having lower hardness and lower oil and grease content provided higher quenching intensity during nucleate boiling but lower quenching intensity during film boiling.

Although a single spray nozzle has been depicted for applying a coolant to the bottom surface of the metallic disk sample, multiple spray nozzles may also be used. In addition, the spray nozzle in conjunction with the flow rate of coolant should be adjusted to ensure that the complete bottom surface of the metallic disk is covered so as to provide accurate quenching intensity data. An exemplary flow rate for a 3 inch diameter metallic disk would include about 8 gallons per hour.

The schematic diagram illustrated in FIG. 2 may also include a filtering means to remove debris and other material from the coolant flow prior to contacting the metallic disk. The filtering means may be any known type and should be constructed such that testing may be performed with or without filtration in the cooling flow.

The coolant temperature used during the measuring process should approximate those temperatures used in actual plant practice. For example, in an aluminum rolling operation, a typical heated coolant would range between 120°-150° F.

As such, an invention has been disclosed in terms of preferred embodiments thereof which fulfill each and every one of the objects of the invention as set forth hereinabove and provides a new and improved apparatus for and method of measuring coolant quenching rates of great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

We claim:
1. A method for measuring coolant quenching rates comprising the steps of:
   a) providing a metallic article having a predetermined thickness;
   b) heating said metallic article to a temperature greater than a predetermined minimum temperature;
   c) insulating said metallic article such that one surface thereof is exposed;
   d) applying a coolant to said one surface;
   e) detecting temperature changes of said metallic article; and
   f) measuring a quenching rate of said coolant by relating said temperature changes detected in step (e) to dimensions and thermal conductivity of said metallic article.

2. The method of claim 1 wherein said step of providing a metallic article further comprises providing a metallic article having a plurality of temperature sensing means aligned along a central axis thereof.

3. The method of claim 1, wherein said step of applying coolant further comprises the additional step of providing a support and barrier means for supporting said metallic article and confining said coolant to said one surface.

4. The method of claim 1, wherein said heating step further comprising heating a surface opposite said one surface.

5. The method of claim 4, wherein said heating step further comprises flame heating said surface opposite said one surface.

6. The method of claim 1 further comprising controlling the said heating of said metallic article responsive to temperatures detected in step (e).

7. The method of claim 1 further comprising the step of detecting pressure of said coolant during step (d) and controlling said application of coolant to said one surface responsive to said detection of pressure.

8. The method of claim 1, wherein said providing step further comprises the step of providing a metallic disk having a top surface, bottom surface and a circumferential side surface.

9. The method of claim 8 wherein said insulating step further comprises the step of providing an insulating material adjacent said side surface and adjacent said top surface such that said bottom surface is exposed.

10. The method of claim 1 wherein said measuring step further comprises the step of calculating a quenching rate based upon the formula:

$$Q = (-k A \text{ (delta } t))/x,$$

wherein Q=heat flow, k is the thermal conductivity of said metallic article, A is the surface area of said one surface, delta t is the temperature gradient along the thickness of said metallic article and x is the metallic article thickness.

11. An apparatus for measuring coolant quenching rates comprising:
   a) a metallic article capable of being heated to a temperature greater than a predetermined minimum temperature where said metallic article is heated by heating means;
   b) insulating means for insulating said metallic article said insulating means adapted to surround said metallic article such that one surface thereof is exposed;
   c) cooling means for applying a coolant to said one surface; and
   d) temperature sensing means for detecting temperature changes in said metallic article;
   e) wherein said temperature changes are related to dimensions and thermal conductivity of said metallic article so as to measure coolant quenching rates for said coolant.

12. The apparatus of claim 11 further comprising flame heating means for heating said metallic article.

13. The apparatus of claim 12 further comprising first control means for controlling said heating means responsive to a temperature of said metallic article.

14. The apparatus of claim 12 wherein said flame heating means further comprises an oxy-acetylene torch.

15. The apparatus of claim 11 wherein said cooling means further comprises:
   i) a coolant reservoir;
   ii) a pump;
   iii) a flow meter and control valve assembly;
   iv) a nozzle for applying coolant to said one surface.

16. The apparatus of claim 15 further comprising pressure sensing means for detecting pressure at said coolant downstream of said flow meter and control valve assembly.

17. The apparatus of claim 16 further comprising second control means for controlling temperature of coolant in said coolant reservoir.

18. The apparatus of claim 11 further comprising support and barrier means for supporting said metallic article and confining said coolant to said one surface of said metallic article.

19. The apparatus of claim 18 wherein said support and barrier means further comprise a refractory tube having low thermal conductivity.

20. The apparatus of claim 11 wherein said insulating means further comprises insulating means for insulating a surface opposite said one surface of said metallic article, and insulating means for insulating a side surface of said metallic article adjacent said one surface.

21. The apparatus of claim 20 wherein said insulating means further comprise Kaowool material.

22. The apparatus of claim 20 wherein said insulating means is removable.

* * * * *